(12) United States Patent
Van Nguyen et al.

(10) Patent No.: US 7,329,268 B2
(45) Date of Patent: Feb. 12, 2008

(54) EXPANDABLE PERCUTANEOUS SHEATH

(75) Inventors: Thanh Van Nguyen, Irvine, CA (US); George P. Teitelbaum, Santa Monica, CA (US); To V. Pham, Trabuco Canyon, CA (US); Samuel M. Shaolian, Newport Beach, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 10/188,732

(22) Filed: Jul. 2, 2002

(65) Prior Publication Data

US 2004/0006344 A1    Jan. 8, 2004

(51) Int. Cl.
*A61M 29/00* (2006.01)

(52) U.S. Cl. ...................................... 606/198

(58) Field of Classification Search ............... 606/1, 606/198; 604/104
See application file for complete search history.

(56) References Cited

U.S. PATENT DOCUMENTS

| | | | |
|---|---|---|---|
| 4,401,433 A | 8/1983 | Luther | |
| 4,451,256 A | 5/1984 | Weikl et al. | |
| 4,710,181 A | 12/1987 | Fuqua | |
| 4,738,666 A | 4/1988 | Fugua | |
| 4,790,817 A | 12/1988 | Luther | |
| 5,073,166 A * | 12/1991 | Parks et al. | 604/175 |
| 5,324,261 A | 6/1994 | Amundson et al. | |
| 5,431,676 A | 7/1995 | Dubrul et al. | |
| 5,507,767 A * | 4/1996 | Maeda et al. | 623/1.2 |
| 5,549,635 A * | 8/1996 | Solar | 623/1.12 |
| 5,647,857 A | 7/1997 | Anderson et al. | |
| 5,817,100 A * | 10/1998 | Igaki | 623/1.11 |
| 5,897,557 A * | 4/1999 | Chin et al. | 606/71 |
| 5,922,019 A * | 7/1999 | Hankh et al. | 623/1.13 |
| 5,964,730 A | 10/1999 | Williams et al. | |
| 6,447,540 B1 | 9/2002 | Fontaine et al. | |
| 6,494,860 B2 | 12/2002 | Rocamora et al. | |
| 6,494,893 B2 | 12/2002 | Dubrul et al. | |
| 2001/0037126 A1 | 11/2001 | Stack et al. | |
| 2002/0010476 A1 | 1/2002 | Mulholland et al. | |
| 2002/0099431 A1* | 7/2002 | Armstrong et al. | 623/1.11 |
| 2004/0073286 A1* | 4/2004 | Armstrong et al. | 623/1.12 |

FOREIGN PATENT DOCUMENTS

WO    US03/020550    7/2003

* cited by examiner

*Primary Examiner*—Michael Thaler
(74) *Attorney, Agent, or Firm*—Goodwin Procter LLP

(57) ABSTRACT

Disclosed is an expandable percutaneous sheath, for introduction into the body while in a first, low cross-sectional area configuration, and subsequent expansion to a second, enlarged cross-sectional configuration. The sheath is maintained in the first, low cross-sectional configuration by a removable tubular restraint. In one application, the sheath is utilized to introduce a formed in place orthopedic fixation rod such as for use in spinal fixation procedures.

32 Claims, 10 Drawing Sheets

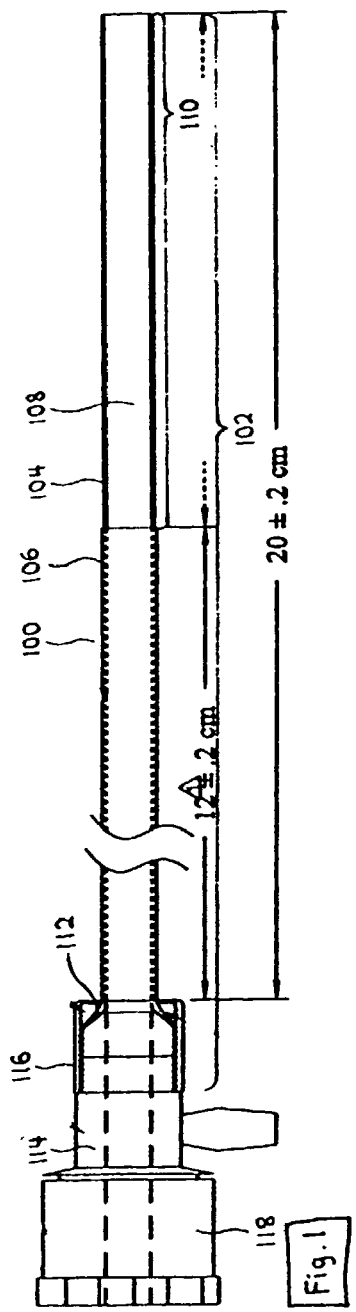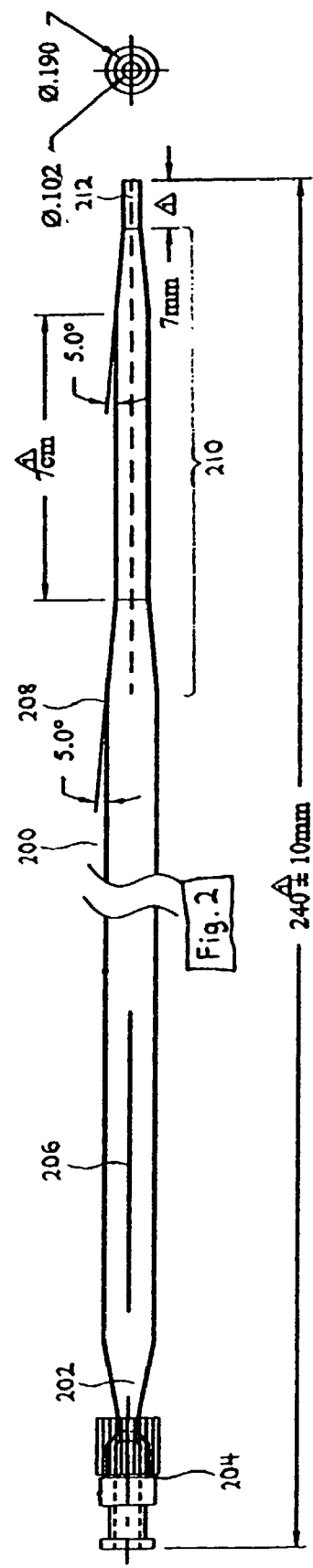

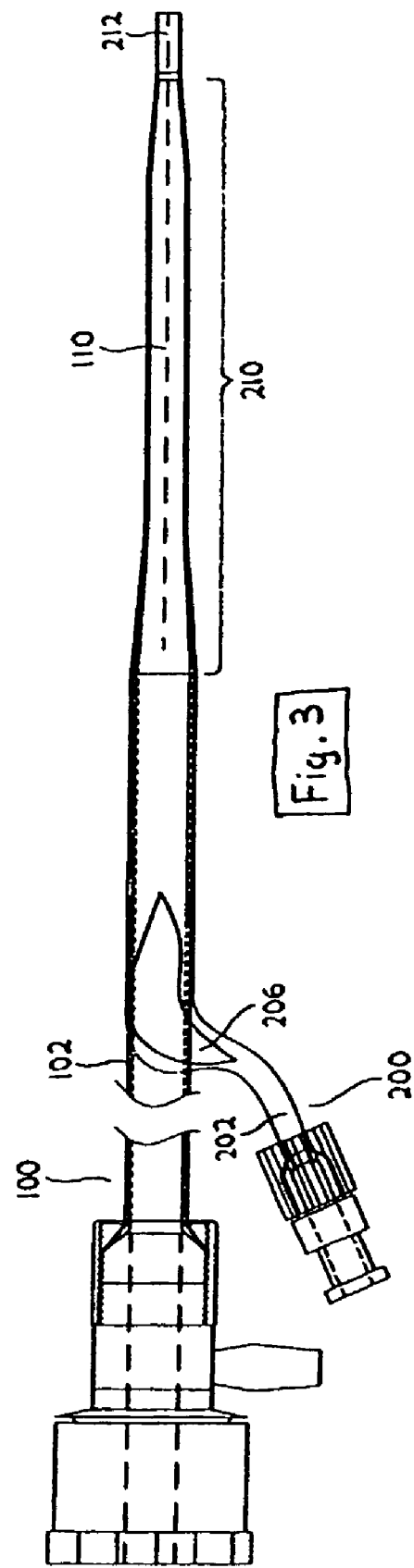

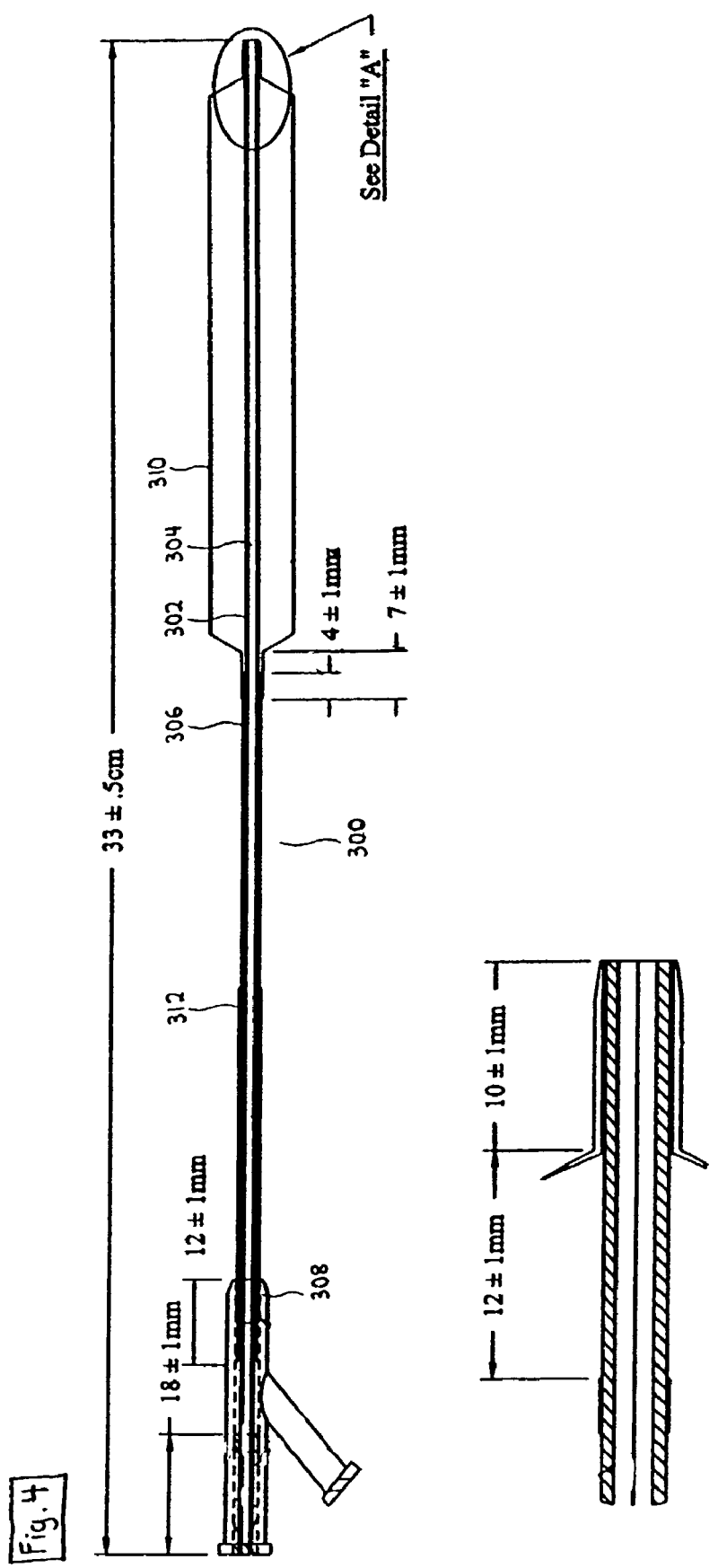

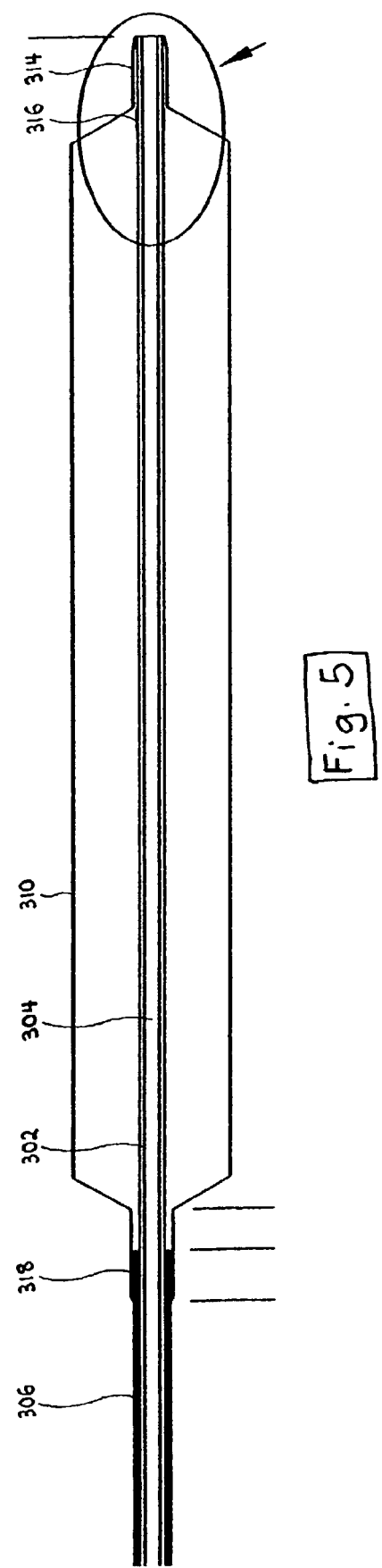

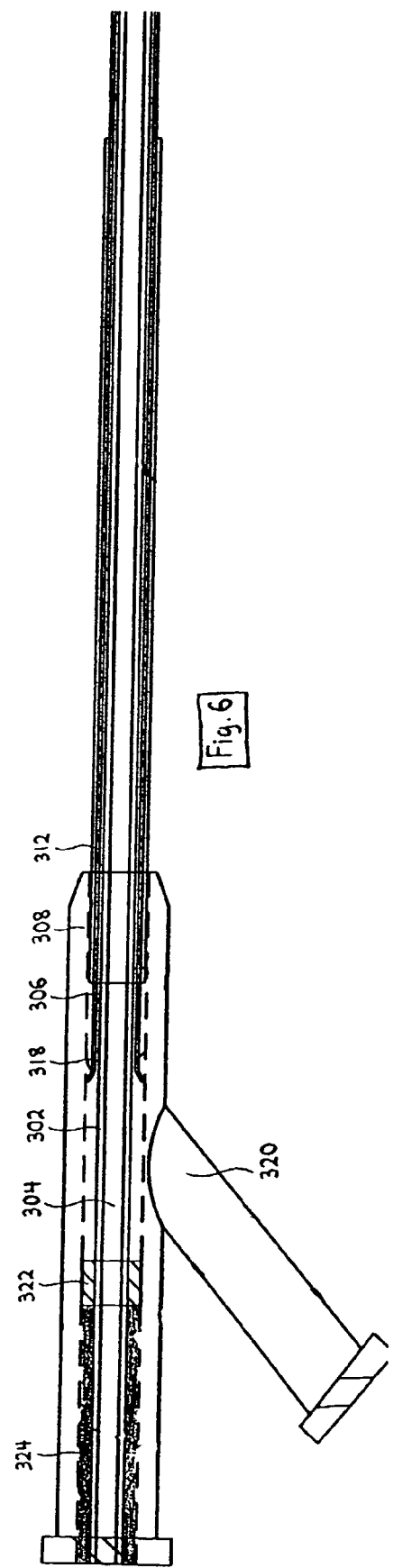

EXPANDABLE PERCUTANEOUS SHEATH

BACKGROUND OF THE INVENTION

1. Field of the Invention

The present invention relates to medical devices and, more particularly, to methods and devices for forming a percutaneous channel. In one application, the present invention relates to a minimally invasive procedure to insert an orthopedic fixation or stabilization implant into the body, such as a formed in situ spinal stabilization rod.

2. Description of the Related Art

The vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed in the prior art. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Therefore, devices and methods are needed for repositioning and fixing displaced vertebrae or portions of displaced vertebrae which cause less pain and potential complications. Preferably, the devices are implantable through a minimally invasive procedure.

In addition, a wide variety of diagnostic or therapeutic procedures involve the introduction of a device through a natural or artificially created access pathway. A general objective of access systems which have been developed for this purpose, is to minimize the cross-sectional area of the puncture, while maximizing the available space for the diagnostic or therapeutic instrument. These procedures include, among others, a wide variety of laproscopic diagnostic and therapeutic interventional procedures. Accordingly, a need remains for access technology which allows a device to be percutaneously passed through a small diameter tissue tract, while accommodating the introduction of relatively large diameter instruments.

SUMMARY OF THE INVENTION

A percutaneous access sheath is provided according to an aspect of the present invention. In one application, the percutaneous access sheath is used to facilitate the insertion of an orthopedic fixation or stabilization implant that is formed in situ, such as a spinal stabilization rod.

The percutaneous access sheath may be used in conjunction with a deployment catheter, which is provided with a balloon at its distal end. The percutaneous access sheath has a proximal section and a variable diameter distal section. The deployment catheter may be disposed within the percutaneous access sheath such that the balloon is positioned within the distal section of the percutaneous access sheath.

The distal section of the percutaneous access sheath is restrained in a first, small diameter by a releasable restraint such as a perforated insertion sheath. The distal section of the percutaneous access sheath is creased, folded inwards and inserted into a distal section of the insertion sheath. This gives the percutaneous access sheath a smaller cross-sectional profile, facilitating its insertion.

The percutaneous access sheath is inserted as packaged above. Following insertion, the insertion sheath may be torn away along its perforations. To facilitate this the balloon may be partially inflated, expanding the distal section of the percutaneous access sheath sufficiently to tear the insertion sheath along its perforations. After the insertion sheath is removed, the balloon may be fully inflated to distend the distal section of the percutaneous access sheath to its full cross-sectional profile. Afterwards, the balloon may be deflated to allow the removal of the deployment catheter, leaving the percutaneous access sheath in place.

In one embodiment where the percutaneous access sheath is used to facilitate the insertion of an orthopedic spinal stabilization implant that is formed in situ, a percutaneous access sheath may advantageously be first inserted through the portals of adjacent bone anchors, by the method described above. This provides a smooth channel to facilitate the passage of another deployment catheter carrying an inflatable orthopedic fixation device at its distal end.

Other applications of the percutaneous access sheath include a variety of diagnostic or therapeutic clinical situations which require access to the inside of the body, through either an artificially created or natural body lumen.

BRIEF DESCRIPTION OF THE DRAWINGS

FIG. 1 is a side elevational view of a percutaneous access sheath.

FIG. 2 is a side elevational view of a insertion sheath.

FIG. 3 illustrates the percutaneous access sheath in a reduced cross-section configuration and inserted into the insertion sheath.

FIG. 4 is a side elevational view of an access sheath expansion catheter.

FIG. 5 is an enlarged view of the distal end of the expansion catheter.

FIG. 6 is an enlarged view of the proximal end of the expansion catheter.

DETAILED DESCRIPTION OF THE PREFERRED EMBODIMENT

Figure 7:
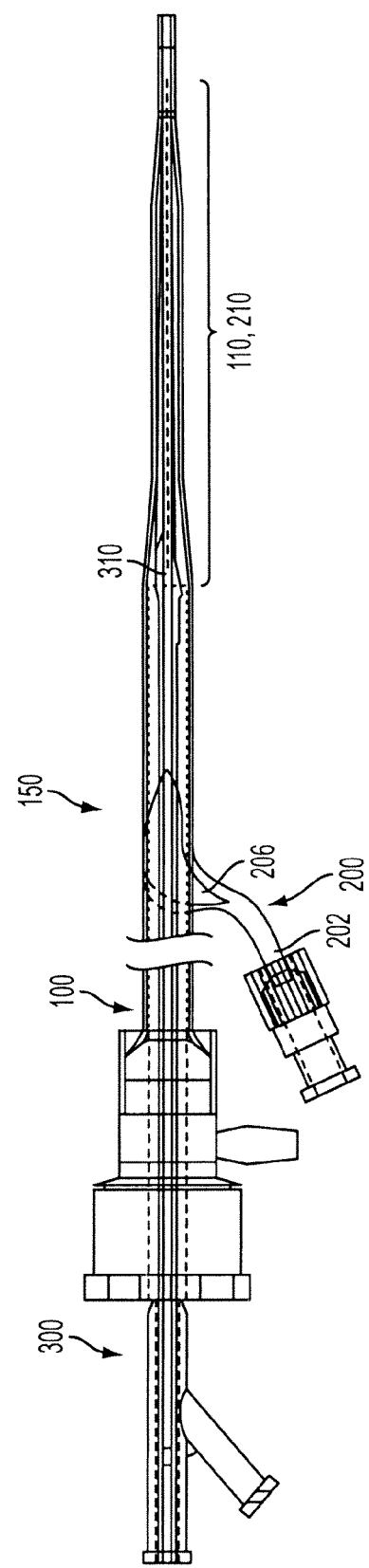
FIG. 7 illustrates the percutaneous access sheath assembly, with the expansion catheter inserted into the structure illustrated in FIG. 3.
Figure 8:
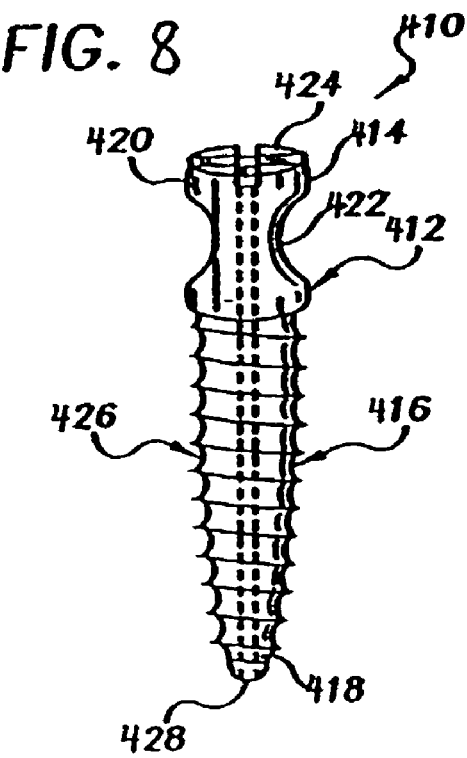
FIG. 8 is a side elevational view of a bone anchor.
Figure 9:
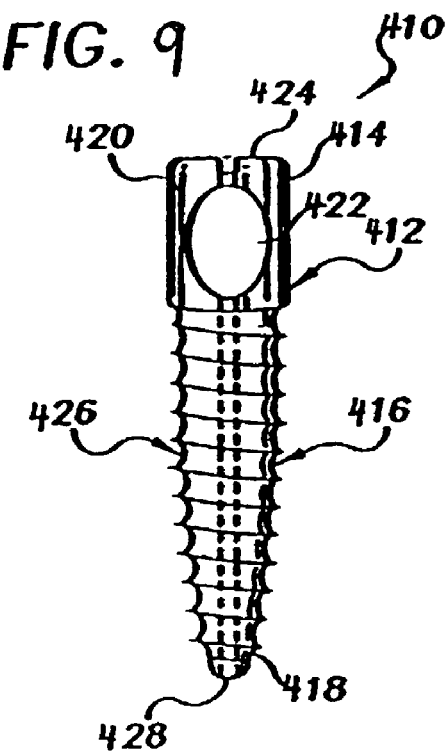
FIG. 9 is a side elevational view of the bone anchor of FIG. 8, rotated 90° about is longitudinal axis.
Figure 10:
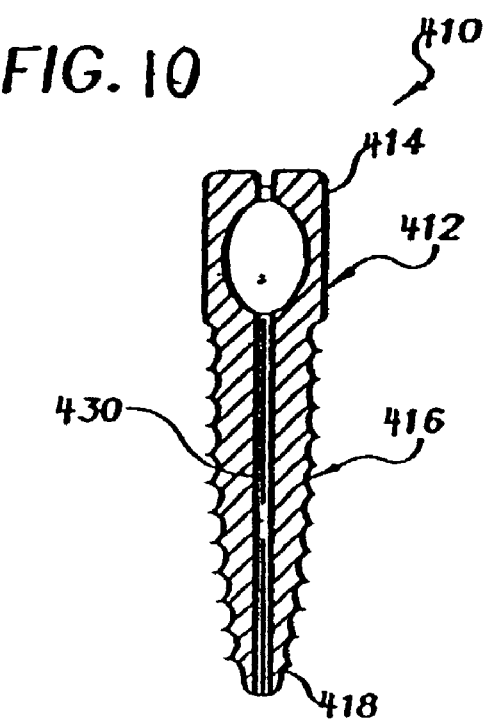
FIG. 10 is a longitudinal cross-sectional view of the bone anchor of FIG. 9.

FIG. 1 is an overview of the percutaneous access sheath 100. It generally comprises an elongate tubular body with an axial lumen, and is designed to provide percutaneous access to a diagnostic or treatment site in the body. The elongate tubular body has a proximal section and a distal section 110. The length of these two sections can be varied according to clinical need, as will be understood by those skilled in the art with reference to this disclosure. The distal section 110 is expandable from a first, smaller cross-sectional profile to a second, larger cross-sectional profile. The first, smaller cross-sectional profile of the distal section 110 eases its insertion into the percutaneous treatment site. After insertion, the distal section 110 is expanded to a second, larger cross-sectional profile to provide a larger passageway for surgical instruments to reach the percutaneous treatment site.

In the illustrated embodiment, the percutaneous access sheath 100 is made of a double-layered co-extruded tubing 102, with an inner layer 104 and an outer layer 106. The inner layer 104 defines a lumen 108. The inner layer 104 extends further distally than the outer layer 106, such that the distal section 110 of the tubing 102 is of a single layer, the inner layer 104. The inner layer 104 may be made of PTFE and the outer layer 106 may be made of HDPE. Other suitable materials, such as nylon, PEBAX or PEEK, may be used for either layer.

In this embodiment, the distal section 110 is creased, folded inwards, and collapsed from a larger to a smaller cross-sectional profile to ease its insertion. As discussed below, in one application of the invention, the distal section 110 is inserted through adjacent bone screws or anchors. Its length is thus determined by the distance between such adjacent bone screws, and is generally in the range of 4-12 cm. The proximal end 112 of the tubing 102 is flared and fitted onto a handle 114. A distal cap 116 may be threaded onto the handle 114 to secure the proximal end 112 of the tubing 102. Additionally a proximal cap 118 may be threaded onto the handle 114. The overall length of the tubing 102 depends on the distance between the insertion and treatment locations, and is generally in the range of 15-60 cm for orthopedic fixation surgery of the vertebrae. In the illustrated embodiment the length of the tubing is approximately 20 cm, with the distal section 110 accounting for approximately half of that length.

FIG. 2 is an overview of the insertion sheath 200. It is preferably made of a thin, smooth and flexible material. The insertion sheath 200 has a proximal section and a distal, restraint section 210. The restraint section 210 has a smaller cross-sectional profile than the proximal section of the insertion sheath 200. The restraint section 210 is adapted to restrain the distal section 110 of the percutaneous access sheath 100 in its smaller cross-sectional profile. This is achieved by inserting the percutaneous access sheath 100 into the insertion sheath 200 such that the distal section 110 of the percutaneous access sheath 100 lies within the restraint section 210 of the insertion sheath 200.

In the illustrated embodiment, the insertion sheath 200 may be made of PTFE. The proximal end 202 of the insertion sheath 200 terminates at a pull tab 204, which may be formed by a threaded luer lock. The insertion sheath 200 is provided with a slit 206 near its proximal end 202. The insertion sheath 200 tapers at a first tapering point 208 into a restraint section 210, which tapers again into the distal tip 212. As discussed above, the restraint section 210 restrains the distal section 110 of the percutaneous access sheath 100 in its smaller cross-sectional profile. Thus the length of the restraint section 210 is approximately the same as or slightly longer than the distal section 110, and generally falls in the range of 4-13 cm.

The diameter of the restraint section 210 is preferably smaller than the diameter of the eye of the bone screw used, as discussed below. The insertion sheath 200 may be perforated or otherwise provided with a tear line distally from the first tapering point 208 to its distal tip 212. The distance between the slit 206 and the distal tip 212 is generally approximately equal to or slightly shorter than the length of the tubing 102, and thus is generally in the range of 12-57 cm. In the illustrated embodiment this distance is approximately 15 cm, and the overall length of the insertion sheath 200 is approximately 24 cm.

FIG. 3 illustrates the percutaneous access sheath 100 inserted into the insertion sheath 200 via the slit 206 provided near its proximal end 202. The diameter of the restraint section 210 of the insertion sheath 200 is smaller than the diameter of the distal section 110 of the tubing 102. The distal section 110 is creased and folded inwards to decrease its effective diameter, and inserted into the restraint section 210. As discussed above, the restraint section 210 restrains the distal section 110 of the percutaneous access sheath 100 in its smaller cross-sectional profile. The restraint section 210 is approximately the same length as or just longer than the distal section 110. Thus inserted, the distal section 110 extends to a point just proximal of the distal tip 212 of the insertion sheath 200.

In certain embodiments an insertion sheath 200 may not be necessary if the distal section 110 of the percutaneous access sheath 100 is made of a stretchable material that may be stretched from a first, smaller cross-sectional profile to a second, larger cross-sectional profile. In these embodiments the outer surface of the distal section 110 is preferably made of a smooth material to facilitate the insertion of the percutaneous access sheath 100 into a treatment site.

FIG. 4 is an overview of the deployment catheter 300. It is provided with an expansion element such as balloon 310 at its distal end. The deployment catheter 300 is inserted into the lumen 108 of the percutaneous access sheath 100 such that the balloon 310 is arranged within the distal section 110. The balloon 310 may be inflated to expand the distal section 110 from its first, smaller cross-sectional profile to its second, larger cross-sectional profile following the insertion of the percutaneous access sheath 100 into a treatment site.

An inner tube 302 extends the entire length of the deployment catheter 300. A guide wire lumen 304 is defined by the interior of the inner tube 302. The deployment catheter 300 can travel along a guide wire extending through the guide wire lumen 304. The inner tube 302 carries coaxially on its exterior an outer tube 306. The outer tube 306 terminates proximally into the distal end of a handle 308, and distally into the proximal end of a balloon 310. The balloon 310 may be made of PET. The handle 308 may be provided with an optional support tube 312 extending from its distal end and over a proximal section of the outer tube 306, to increase the rigidity of the deployment catheter 300 during insertion. This support tube 312 may be made of aluminum.

FIG. 5 is an enlarged view of the distal end of the deployment catheter 300. Both the inner tube 302 and the guide wire lumen 304 extend through the distal end 314 of the balloon 310. The inner tube 302 carries coaxially on its exterior a marker ring 316 near the distal end 314 of the balloon 310. Alternatively the marker ring 316 may be carried by the distal end 314 of the balloon 310. The marker ring 316 is preferably made of gold, tantalum, or another radio-opaque material. Additional marker rings may be provided in the balloon 310 to aid in visualizing its location. A balloon inflation lumen 318, defined in the space between the inner tube 302 and the outer tube 306, communicates with the interior of the balloon 310. As discussed above, the balloon 310 may be inflated to expand the distal section 110 of the percutaneous access sheath 100 from its first, smaller cross-sectional profile to its second, larger cross-sectional profile. Thus the length of the balloon 310 is approximately equal to or slightly longer than the length of the distal section 110. In the illustrated embodiment the length of the balloon 310 is approximately 10 cm.

FIG. 6 is an enlarged view of the proximal end of the deployment catheter 300. Both the inner tube 302 and the guide wire lumen 304 extend through the proximal end of the handle 308. The balloon inflation lumen 318, defined in the space between the inner tube 302 and the outer tube 306, opens into a port 320 in the handle 308. A stopper 322 supports the inner tube 302 within the handle 308 and prevents the balloon inflation lumen 318 from communicating with the space 324 in the main branch of the handle 308. Thus only the port 320 communicates via the balloon inflation lumen 318 with the interior of the balloon. A pump may be connected to the port 320 to inflate or deflate the balloon. To enable visualization of the state of the balloon, it may be inflated with contrast media.

FIG. 7 illustrates the percutaneous access sheath assembly 150. The percutaneous access sheath assembly 150 comprises the percutaneous access sheath 100, the insertion sheath 200 and the deployment catheter 300. It is assembled by inserting the deployment catheter 300 into the percutaneous access sheath 100 and inserting the percutaneous access sheath 100 into the insertion sheath 200 such as via the slit 206 or other proximal opening provided near its proximal end 202. The balloon 310 of the deployment catheter 300 is deflated, folded and inserted into the distal section 110 of the access sheath 100. The distal section 110, as discussed above, is creased and folded inwards to decrease its effective diameter, and inserted into the restraint section 210 of the insertion sheath 200. As discussed, the balloon 310 is approximately the same length as or just longer than the distal section 110 and the restraint section 210.

FIGS. 8-11 illustrate one embodiment of a bone anchor 410 as mentioned above. It is provided with at least one connector 422 at or near its proximal end (or top end, as illustrated). This connector 422 is used to engage an orthopedic spinal stabilization implant that is formed in situ, as discussed below. The connector 422 is preferably an aperture 422, to achieve a more secure engagement. In one embodiment the percutaneous access sheath 100 extends through the apertures 422 of two or more bone anchors 410 to establish a passageway to facilitate the insertion of a formed in situ orthopedic spinal stabilization implant.

An embodiment with two bone anchors is now described. The percutaneous access sheath 100 is extended through the aperture 422 of a first bone anchor 410, then through the aperture 422 of a second bone anchor 410. The first bone anchor 410 is preferably implanted within a first bone. The second bone anchor 410 may be implanted within the second bone. The bones may be adjacent vertebral bodies or vertebrae, or first and second vertebrae spaced apart by one or more intermediate vertebrae. The clinical procedure is described in further detail below.

The bone anchors 410 of FIGS. 8-11 are made of a biocompatible material such as titanium or stainless steel. Alternatively, the bone anchors 410 may be made of a composite material. The bone anchors 410 may also be made of a suitable medical grade polymer. In one embodiment, the bone anchors 410 have a length between about 40 mm and 60 mm, preferably about 50 mm. However, the actual length is dependent on the location of the fracture, size of patient, etc.

The bone anchor 410 comprises a proximal portion 412 having a proximal end 414 and a distal portion 416 having a distal end 418. The proximal portion 412 typically comprises a head 420 and a portal 422. In a preferred embodiment, the head 420 comprises a proximal portion 424 configured to mate with the tip of a screwdriver. The head 420 may comprise a standard or Phillips slot for mating with the screwdriver. A variety of slot configurations are also suitable, such as hexagonal, Torx, rectangular, triangular, curved, or any other suitable shape. The bone anchor of FIG. 11 has a raised platform 434 having a plurality of substantially flat sides, such as a hexagonal platform, configured to mate with a corresponding depression in the distal end of a screwdriver. Platform 434 may come in a variety of shapes suitable mating with a screwdriver.

The portal 422 of the bone anchor 410 may extend through the head 420 and is generally between about 4 mm and 8 mm in diameter, preferably about 6 mm to about 8 mm in diameter. The portal 422 may be of any suitable shape; however, the portal 422 is preferably round to facilitate the insertion of the percutaneous tube 100 as well as the in situ forming orthopedic spinal stabilization implant.

Figure 11:
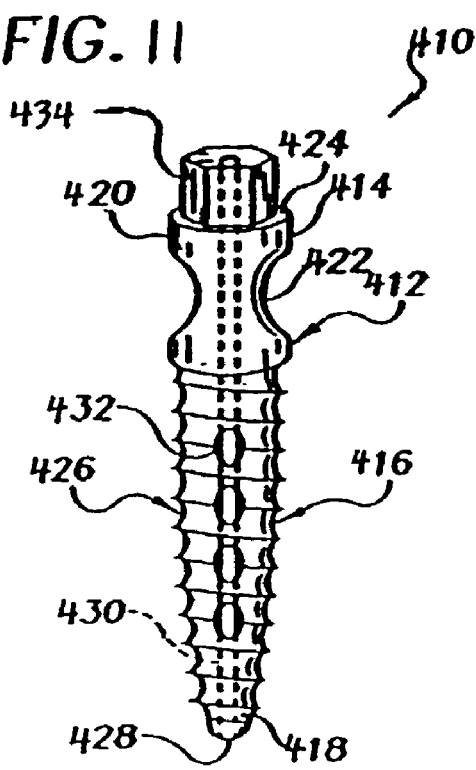
FIG. 11 is a side elevational view of an alternative embodiment of a bone anchor.

The distal portion 416 of the bone anchor 410 typically comprises threads 426 and a sharp tip 428. The bone anchor 410 also preferably comprises a central lumen 430 extending coaxially through the length of the bone anchor 410 from its proximal end 414 to its distal end 418 and configured to receive a guidewire. The bone anchor 410 may also include one or more perforations 432, as shown in FIG. 11. These perforations 432 are in communication with the central lumen 430 of the bone anchor 410. The perforations 432 may be aligned axially, as illustrated, or may be staggered axially. The perforations 432 permit bone to grow into bone anchor 410, stabilizing bone anchor 410 within the bone. Additionally, bone matrix material such as a hydroxyapatite preparation can be injected into the central lumen 430 and through the perforations 432 to promote bone in-growth.

The method of using the percutaneous access sheath 100 to facilitate the insertion of an orthopedic spinal stabilization implant formed in situ according to one aspect of the present invention is described in the following figures. In this embodiment a smooth channel is first established between two or more adjacent bone anchors to facilitate the passage of another deployment catheter carrying an inflatable orthopedic fixation device at its distal end. While the method is disclosed and depicted with reference to only two vertebrae, one of which is either unstable, separated or displaced and the other of which is neither unstable, separated or displaced, the method can also be applied to three or more vertebrae simultaneously. Further, the method can be used to stabilize the L5 vertebrae, using the cranial-ward portion of the sacrum as the "vertebrae" with which L5 is anchored. Although the method is disclosed and depicted as applied on the left side of the vertebral column, the method can also be applied on the right side of the vertebral column or, preferably, on both sides of the vertebral column, as will be understood by those skilled in the art with reference to this disclosure. Other applications include the stabilization of other bones and skeletal elements of the body.

Figure 12:
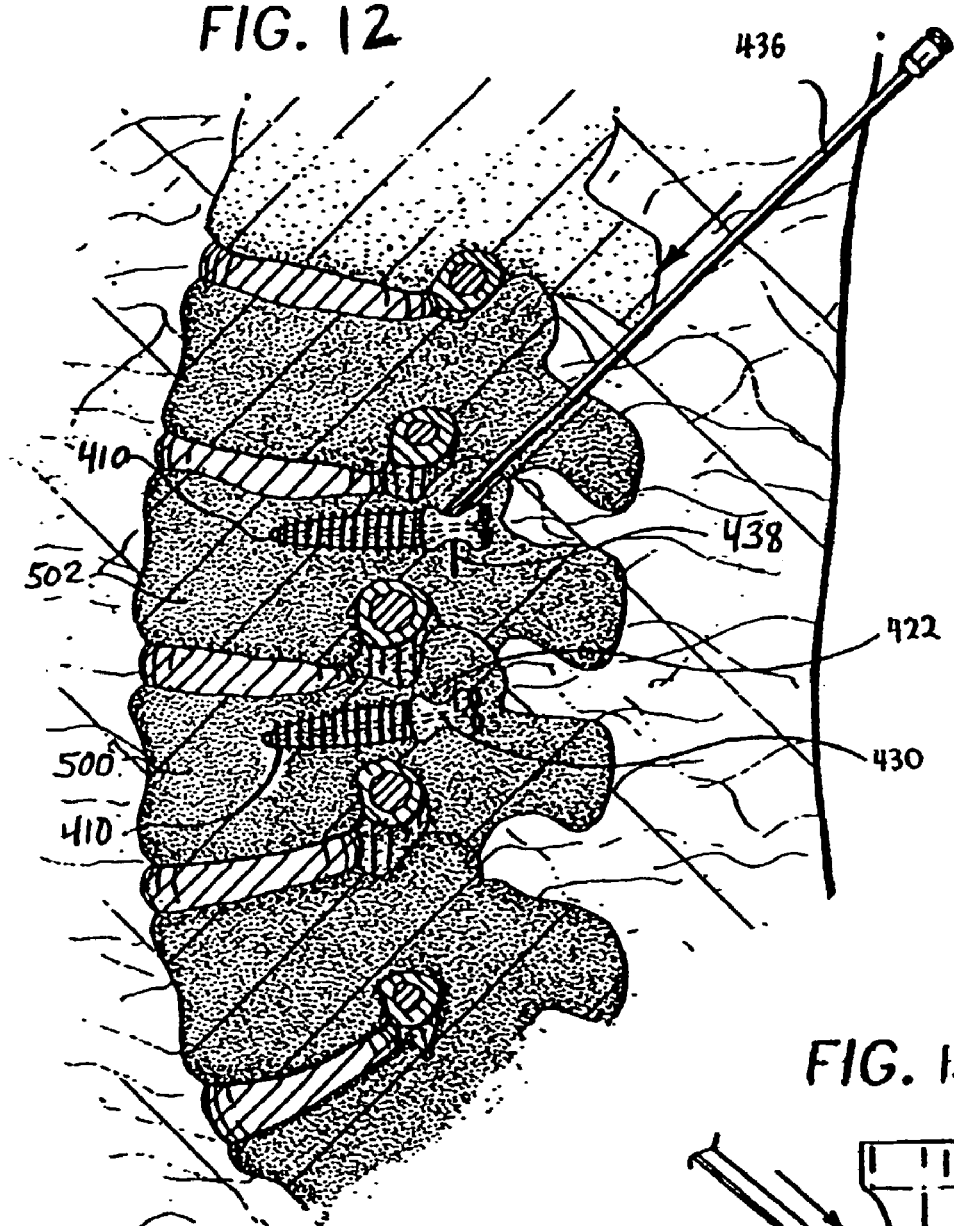
FIG. 12-15 illustrate one embodiment of a method of threading a guide wire through the portals of bone anchors that have been implanted into adjacent vertebrae in a vertebral column.

FIG. 12 illustrates bone anchors 410 that have been inserted through the periosteal surface and into the anterior vertebral body or another suitable portion of the vertebrae 500 and 502. As discussed above, bone matrix material such as a hydroxyapatite preparation can be injected into the central lumen 430 of a bone anchors 410 and through its perforations (not visible in this figure) to promote bone in-growth. The bone anchors 410 are arranged such that their portals 422 are substantially coaxial in relation to each other.

Figure 13:
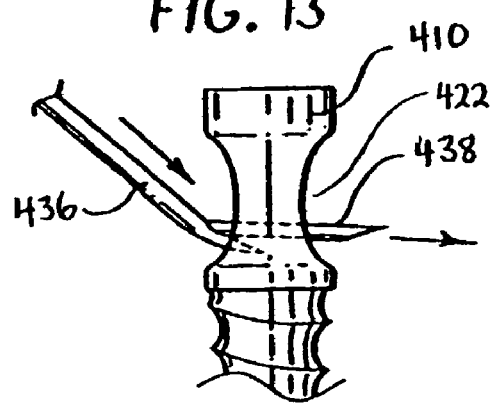

A hollow needle 436 is inserted percutaneously and advanced into the portal 422 of one of the bone anchors 410, with the aid of fluoroscopy. The hollow needle 436 may be 16 or 18 gauge. While the hollow needle 436 is shown engaging the bone screw 410 in the cranial-ward vertebrae 502, it can alternatively first engage the bone screw 410 in the caudal-ward vertebrae 500, as will be understood by those skilled in the art with reference to the disclosure. FIG. 13 is an enlarged view of the distal end of the hollow needle 436. A semi-rigid guide wire 438 is introduced through the lumen of the hollow need 436 and the portal 422 of the bone anchor 410 in the cranial-ward vertebrae 502. The hollow needle 436 preferably has a Tuohy needle tip which causes the guide wire 438 to exit the hollow needle 436 perpendicularly to the central lumen 430 of the bone anchor 410, or coaxially with the axis of the portal 422 of the bone anchor 410. Alternatively, the bending of the guide wire 438 through the portal 422 of the bone anchor 410 may be accomplished by an angled-tip modified Ross needle or another suitable structure as will be understood by those skilled in the art with reference to the disclosure.

Figure 14:
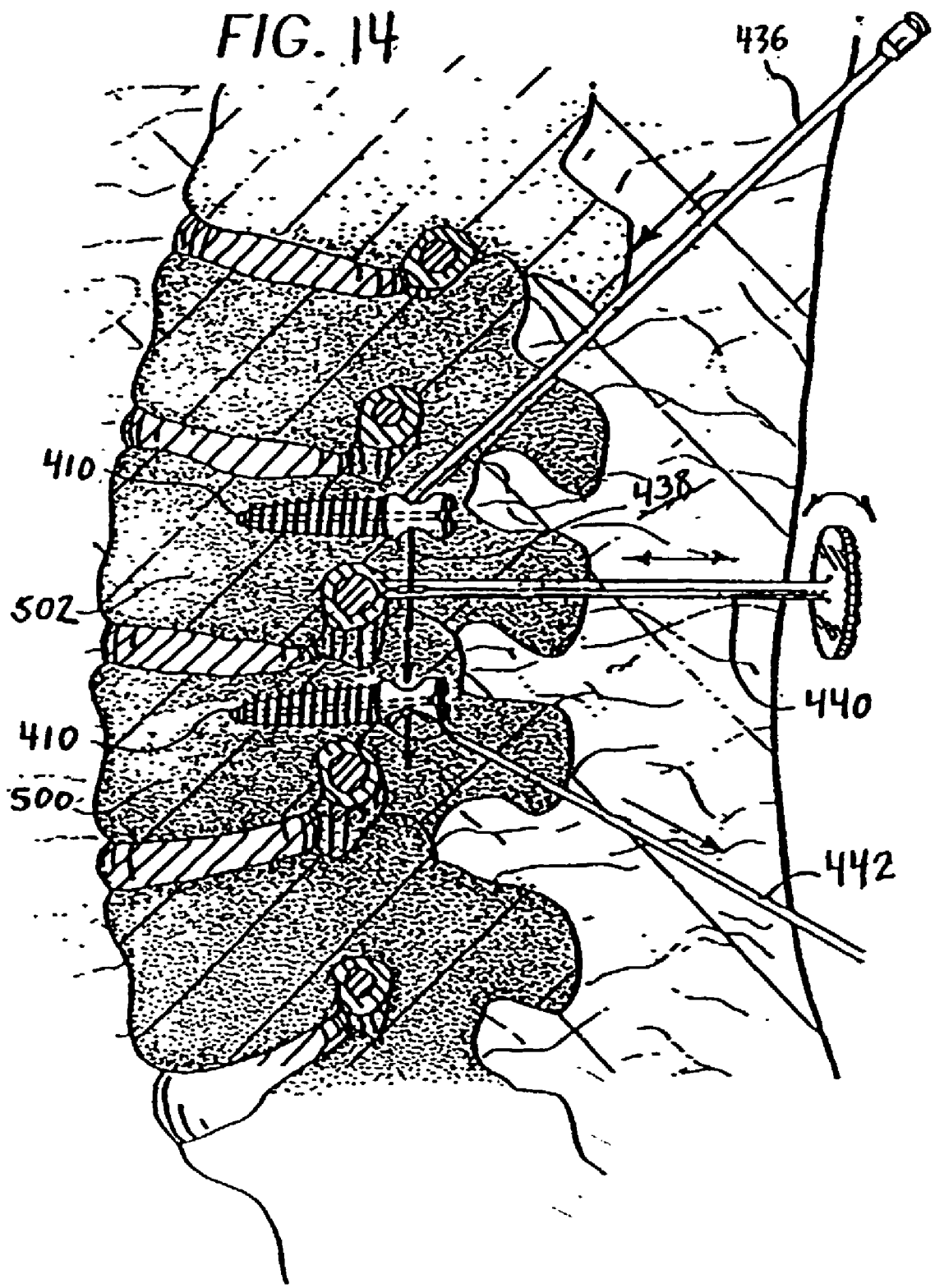

FIG. 14 illustrates an optional guide wire directing device 440, according to one aspect of the present invention, inserted percutaneously between the bone anchors 410. The guide wire directing device 440 may have a forked end used to direct the guide wire 438 through the portal 422 of the bone anchor 410 in the caudal-ward vertebrae 500. In another embodiment a guide wire capture device 442, such as a snare or forceps, may be inserted percutaneously caudal to the portal 422 of the bone anchor 410 in the caudal-ward vertebrae 500. The guide wire capture device 442 engages the distal end of the guide wire 438 after the guide wire 438 has passed through portal 422 of the bone anchor 410 in the caudal-ward vertebrae 500, and pulls it through the skin dorsally, so that both ends of the guide wire 438 are secured.

Figure 15:
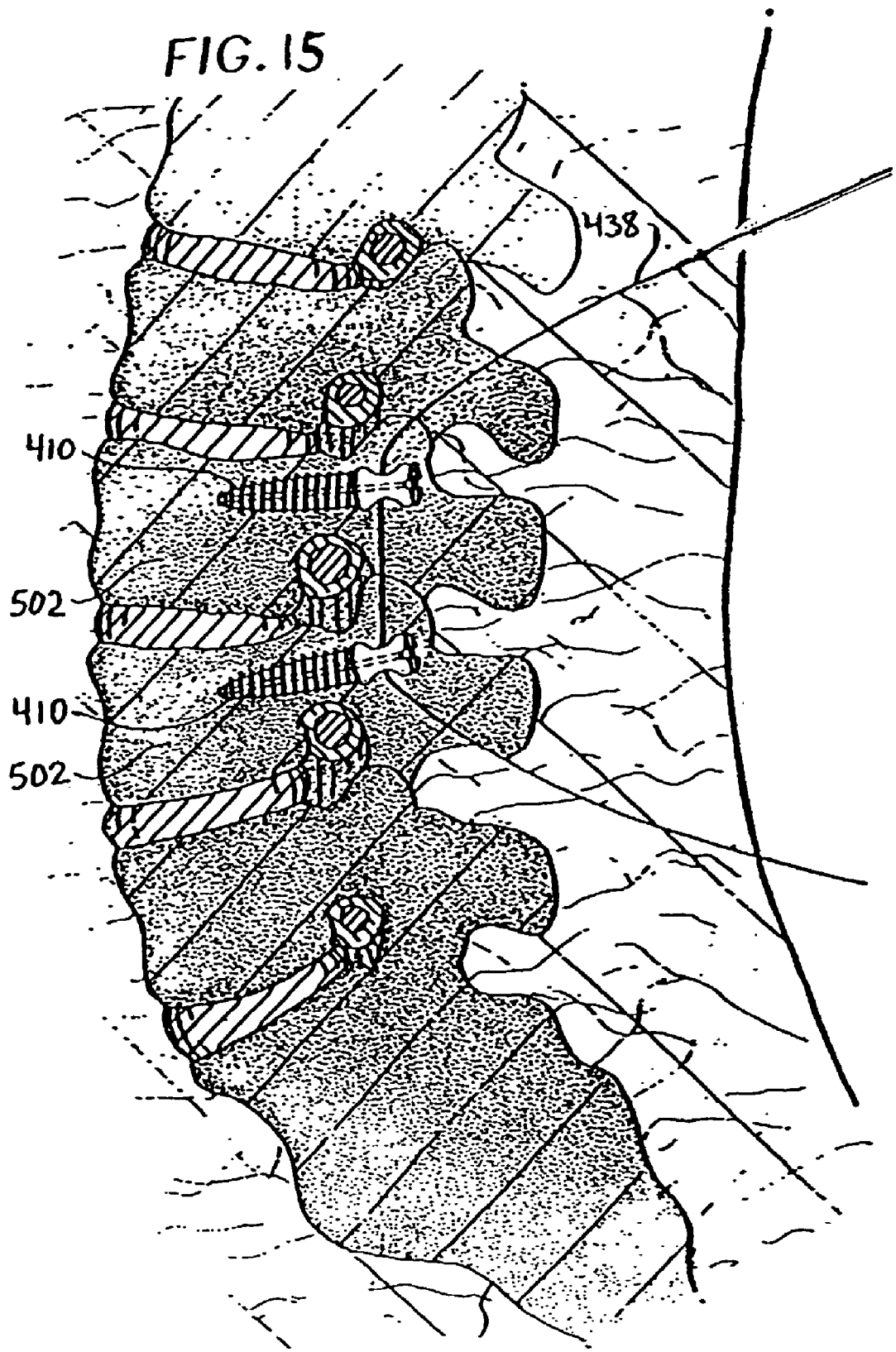

FIG. 15 illustrates the guide wire 438 in place after the procedure described above in FIGS. 12-14.

The guide wire 438 may be inserted into the guide wire lumen 304 of the deployment catheter 300 of the percutaneous access sheath assembly 150. The entire assembly 150 may travel over the guide wire 438 until its distal tapered portion is inserted through the portals 422 of the bone anchors 410. The insertion sheath 200, which is on the exterior of the percutaneous access sheath assembly 150, facilitates the insertion because of its smooth, low profile exterior. As discussed above, it may be made of PTFE.

Following the insertion of the percutaneous access sheath assembly 150, the insertion sheath 200 is removed. This may be accomplished by pulling on the pull tab 204 and tearing the insertion sheath 200 along the perforations, crease line, or other structure for facilitating tearing provided along its restraint section 210. This may be facilitated by first partially inflating the balloon 310 of the deployment catheter 300. As discussed above, the balloon 310 is arranged within the distal section 110 of the percutaneous access sheath 100, which is itself arranged within the restraint section 210 of the insertion sheath 200. Thus, inflating the balloon 310 causes the distal section 110 of the percutaneous access sheath 100 to expand, tearing the restraint section 210 of the insertion sheath 200 along its perforations.

After the removal of the insertion sheath 200, the balloon 310 may be fully inflated to expand the distal section 110 of the percutaneous access sheath to its full cross-sectional profile. Afterwards the balloon 310 may be deflated to ease the removal of the deployment catheter 300. As discussed above, the inflation and deflation of the balloon 310 may be done via a pump connected to the port 320 of the deployment catheter 300, and preferably with contrast media being pumped, to better convey the state of the balloon.

Thus the percutaneous access sheath 100 is inserted through the portals 422 of the bone anchors 410. The establishment of this smooth channel through the portals 422 of the bone anchors 410 facilitates the passage of another deployment catheter carrying an inflatable orthopedic fixation device at its distal end. An example of such a deployment catheter with an inflatable orthopedic fixation device at its distal end as well as the associated anchors and methods are disclosed in U.S. patent application Ser. No. 10/161,554 filed on May 31, 2002, the disclosure of which is hereby incorporated by reference in its entirety.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A percutaneous access sheath assembly comprising:
   an elongate tubular structure, a first portion of said elongate tubular structure being expandable from a first cross-sectional profile to a second cross-sectional profile;
   a releaseable sheath further comprising:
      a proximal end;
      a restraint section;
      a distal end; and
      a first tapering point located at a transition between said proximal end and said restraint section, said first tapering point causing a reduction in the cross-sectional profile of said releaseable sheath to a smaller cross-sectional profile of said restraint section and wherein said restraint section restrains at least a portion of said first portion in said first cross-sectional profile; and
   a balloon positionable inside said elongate tubular structure, wherein inflation of the balloon causes at least a portion of said first portion to expand said restraint section of the releaseable sheath to tear, and the balloon is removable from said elongate tubular structure after it has expanded and at least partially deflated;
   wherein the first tapering point is present before said balloon is inflated.

2. The percutaneous access sheath assembly of claim 1, wherein the balloon is carried by a balloon catheter.

3. A surgical access assembly comprising:
a percutaneous access sheath, the percutaneous access sheath comprising a first longitudinal portion and a second longitudinal portion, the first longitudinal portion having an inner layer and an outer layer, the second longitudinal portion having only the inner layer, the inner layer extending longitudinally out and away from the outer layer at the intersection of the first longitudinal portion and the second longitudinal portion, the inner layer being folded into a reduced cross-sectional profile along at least part of the length of the second longitudinal portion;
a removable insertion sheath surrounding at least part of the second longitudinal portion, the removable insertion sheath further comprising:
a proximal section;
a restraint section;
a distal section; and
a first tapering point located at a transition between said proximal section and said restraint section, said first tapering point causing a reduction in the cross-sectional profile of said removable insertion sheath to a smaller cross-sectional profile of said restraint section and wherein said restraint section retains a portion of the inner layer in its reduced cross-sectional profile, the removable insertion sheath being removable from the percutaneous access sheath by the surgeon after insertion of the percutaneous access sheath and the removable insertion sheath into the patient; and
a balloon longitudinally positionable by the surgeon inside the percutaneous access sheath, the balloon positioned inside the second longitudinal portion and inflatable to a cross-sectional profile that tears at least a portion of the removable insertion sheath and exceeds the reduced cross-sectional profile of the inner layer;
wherein the first tapering point is present before said balloon is inflated.

4. The surgical access assembly of claim 3 wherein:
the restraint section surrounds a portion of the second longitudinal portion of the percutaneous access sheath and retains a portion of the inner layer in its reduced cross-sectional profile and the proximal section surrounds a portion of the first longitudinal section of the percutaneous access sheath.

5. The surgical access assembly of claim 4 further comprising:
a deployment balloon catheter, wherein the balloon is provided on the deployment balloon catheter; and
wherein the percutaneous access sheath defines an axial lumen and the deployment balloon catheter is longitudinally positionable inside the axial lumen of the percutaneous access sheath.

6. The surgical access assembly of claim 5 wherein the deployment balloon catheter comprises:
an inner tube and an outer tube, a portion of the outer tube forming the balloon; and
an inflation lumen between the inner tube and outer tube for inflating the balloon.

7. The surgical access assembly of claim 6 wherein the deployment balloon catheter further comprises:
a guide wire lumen defined by an inner surface of the inner tube.

8. The surgical access assembly of claim 7 wherein a guide wire is positioned in the guide wire lumen and the surgical access assembly is slidable along the guide wire to be directed to a surgical site in a patient.

9. The surgical access assembly of claim 3 further comprising:
a deployment balloon catheter, wherein the balloon is provided on the deployment balloon catheter; and
wherein the percutaneous access sheath defines an axial lumen and the deployment balloon catheter is longitudinally positionable inside the axial lumen of the percutaneous access sheath.

10. The surgical access assembly of claim 9 wherein the deployment balloon catheter comprises:
an inner tube and an outer tube, a portion of the outer tube forming the balloon; and
an inflation lumen between the inner tube and outer tube for inflating the balloon.

11. The surgical access assembly of claim 10 wherein the deployment balloon catheter further comprises:
a guide wire lumen defined by an inner surface of the inner tube.

12. The surgical access assembly of claim 11 wherein a guide wire is positioned in the guide wire lumen and the surgical access assembly is slidable along the guide wire to be directed to a surgical site in a patient.

13. A surgical access assembly comprising:
a percutaneous access sheath, the percutaneous access sheath comprising a first longitudinal portion and a second longitudinal portion, the second longitudinal portion being expandable from a first, reduced cross-sectional profile to a second, greater cross-sectional profile;
a removable insertion sheath surrounding at least part of the second longitudinal portion, the removable insertion sheath further comprising:
a proximal section;
a restraint section;
a distal section; and
a first tapering point located at a transition between said proximal section and said restraint section, said first tapering point causing a reduction in the cross-sectional profile of said removable insertion sheath to a smaller cross-sectional profile of said restraint section and wherein said restraint section retains the second longitudinal portion in its first, reduced cross-sectional profile, the removable insertion sheath being removable from the percutaneous access sheath by the surgeon after insertion of the percutaneous access sheath and the removable insertion sheath into the patient; and
a balloon longitudinally positionable by the surgeon inside the percutaneous access sheath, the balloon positioned inside the second longitudinal portion and inflatable to a cross-sectional profile that tears at least a portion of the removable access sheath and exceeds the second, reduced cross-sectional profile of the second longitudinal portion;
wherein the first tapering point is present before said balloon is inflated.

14. A surgical access assembly comprising:
a percutaneous access sheath, the percutaneous access sheath comprising a first longitudinal portion and a second longitudinal portion, the first longitudinal portion having an inner layer and an outer layer, the second longitudinal portion having only the inner layer, the inner layer extending longitudinally out and away from the outer layer at the intersection of the first longitudinal portion and the second longitudinal portion, the inner layer being folded into a reduced cross-sectional profile along at least part of the length of the second longitudinal portion;

a removable insertion sheath surrounding at least part of the second longitudinal portion, the removable insertion sheath further comprising:
  a proximal section;
  a restraint section;
  a distal section; and
  a first tapering point located at a transition between said proximal section and said restraint section, said first tapering point causing a reduction in the cross-sectional profile of said removable insertion sheath to a smaller cross-sectional profile of said restraint section and wherein said restraint section retains a portion of the inner layer in its reduced cross-sectional profile, the removable insertion sheath being removable from the percutaneous access sheath by the surgeon after insertion of the percutaneous access sheath and the removable insertion sheath into the patient; and a balloon longitudinally positionable by the surgeon inside the percutaneous access sheath, the balloon having a length substantially equal to about a length of the second longitudinal portion, the balloon positioned inside the second longitudinal portion and inflated to a cross-sectional profile that exceeds the reduced cross-sectional profile of the inner layer;

wherein the first tapering point is present before said balloon is inflated.

15. A surgical access assembly for use in percutaneous spinal surgery comprising:
  a percutaneous access sheath having a first portion and a second portion, the first portion having an inner layer and an outer layer, the second portion having the inner layer, the inner layer extending longitudinally from the outer layer at an intersection of the first portion and the second portion, the inner layer adapted to have a first cross-sectional profile along at least part of a length of the second portion;
  an insertion sheath releasably housing at least a portion of the second portion, the insertion sheath further comprising:
    a proximal section;
    a restraint section;
    a distal section; and
    a first tapering point located at a transition between said proximal section and said restraint section, said first tapering point causing a reduction in the cross-sectional profile of said insertion sheath to a smaller cross-sectional profile of said restraint section and wherein said restraint section retains a portion of the inner layer in the first cross-sectional profile, the insertion sheath being removable from the percutaneous access sheath after insertion of the surgical access assembly into a patient during percutaneous spinal surgery; and
  an inflatable member positionable inside the percutaneous access sheath, the inflatable member positioned inside the second portion and inflated to a second cross-sectional profile wherein said second cross-sectional profile is greater than said first cross-sectional profile;
  wherein the first tapering point is present before said inflatable member is inflated.

16. The surgical access assembly of claim 15 further comprising:
  a deployment catheter wherein the inflatable member is positionable in the deployment catheter, and
  wherein the percutaneous access sheath defines an axial lumen and the deployment catheter is positionable inside the axial lumen of the percutaneous access sheath.

17. The surgical access assembly of claim 16 wherein the deployment catheter comprises:
  an inner tube and an outer tube, a portion of the outer tube forming the inflatable member; and
  an inflation lumen positioned between the inner tube and the outer tube for inflating the inflatable member.

18. The surgical access assembly of claim 17 wherein the deployment catheter further comprises:
  a guide wire lumen defined by an inner surface of the inner tube.

19. The surgical access assembly of claim 18 wherein a guide wire is positioned in the guide wire lumen and the surgical access assembly is slidable along the guide wire to be directed to a surgical site in the patient.

20. A surgical access assembly for use in percutaneous spinal surgery comprising:
  a percutaneous access sheath having a first portion and a second portion, the first portion having an inner layer and an outer layer, the second portion having the inner layer, the inner layer extending longitudinally from the outer layer at an intersection of the first portion and the second portion, the inner layer adapted to have a first cross-sectional profile along at least part of a length of the second portion;
  an insertion sheath releasably housing at least a portion of the second portion, the insertion sheath further comprising:
    a proximal section;
    a restraint section;
    a distal section; and
    a first tapering point located at a transition between said proximal section and said restraint section, said first tapering point causing a reduction in the cross-sectional profile of said insertion sheath to a smaller cross-sectional profile of said restraint section and wherein said restraint section retains a portion of the inner layer in the first cross-sectional profile, the insertion sheath being removable from the percutaneous access sheath after insertion of the surgical access assembly into a patient during percutaneous spinal surgery;
  a deployment catheter positionable inside the percutaneous access sheath, the deployment catheter having an inflatable member and a guide wire lumen, the inflatable member of the deployment catheter positioned inside the second portion and inflated to a second cross-sectional profile wherein said second cross-sectional profile is greater than.said first cross-sectional profile; and
  a guide wire positioned in the guide wire lumen, where the surgical access assembly is movable along the guide wire to be directed to a surgical site in the patient;
  wherein the first tapering point is present before said inflatable member is inflated.

21. A surgical access assembly for use in percutaneous spinal surgery comprising:
  a percutaneous access sheath having a first portion and a second portion, the first portion having an inner layer and an outer layer, the second portion having the inner layer, the inner layer extending longitudinally from the outer layer at an intersection of the first portion and the second portion, the inner layer adapted to have a first cross-sectional profile along at least part of a length of the second portion;

an insertion sheath releasably housing at least a portion of the second portion, the releasable sheath having at least one perforation, the insertion sheath further comprising:
a proximal section;
a restraint section;
a distal section; and
a first tapering point located at a transition between said proximal section and said restraint section, said first tapering point causing a reduction in the cross-sectional profile of said insertion sheath to a smaller cross-sectional profile of said restraint section and wherein said restraint section retains a portion of the inner layer in the first cross-sectional profile; and
an inflatable member positionable inside the percutaneous access sheath, the inflatable member positioned inside the second portion and inflated to a second cross-sectional profile wherein said second cross-sectional profile is greater than said first cross-sectional profile;
wherein the first tapering point is present before said inflatable member is inflated.

22. The surgical access assembly of claim 21 wherein the insertion sheath being adapted to tear along the at least one perforation to assist the removal of the insertion sheath from the percutaneous access sheath after insertion of the surgical access assembly into a patient.

23. The surgical access assembly of claim 21 further comprising:
a deployment catheter wherein the inflatable member is positionable in the deployment catheter, and
wherein the percutaneous access sheath defines an axial lumen and the deployment catheter is positionable inside the axial lumen of the percutaneous access sheath.

24. The surgical access assembly of claim 23 wherein the deployment catheter comprises:
an inner tube and an outer tube, a portion of the outer tube forming the inflatable member; and
an inflation lumen positioned between the inner tube and the outer tube for inflating the inflatable member.

25. The surgical access assembly of claim 24 wherein the deployment catheter further comprises:
a guide wire lumen defined by an inner surface of the inner tube.

26. The surgical access assembly of claim 25 wherein a guide wire is positioned in the guide wire lumen and the surgical access assembly is slidable along the guide wire to be directed to a surgical site in the patient.

27. A surgical access assembly comprising:
a percutaneous access sheath having a first portion and a second portion, the first portion having an inner layer and an outer layer, the second portion having the inner layer, the inner layer extending longitudinally from the outer layer at an intersection of the first portion and the second portion, the inner layer adapted to have a first cross-sectional profile along at least part of a length of the second portion;
an insertion sheath releasably housing at least a portion of the second portion, the insertion sheath further comprising:
a proximal section;
a restraint section;
a distal section; and
a first tapering point located at a transition between said proximal section and said restraint section, said first tapering point causing a reduction in the cross-sectional profile of said insertion sheath to a smaller cross-sectional profile of said restraint section and wherein said restraint section retains a portion of the inner layer in the first cross-sectional profile, the insertion sheath being removable from the percutaneous access sheath after insertion of the surgical access assembly into a patient;
a deployment catheter positionable inside the percutaneous access sheath, the deployment catheter having an inflatable member and a guide wire lumen, the inflatable member of the deployment catheter positioned inside the second portion and inflated to a second cross-sectional profile wherein said second cross-sectional profile is greater than said first cross-sectional profile; and
a guide wire positioned in the guide wire lumen, where the surgical access assembly is movable along the guide wire to be directed to a surgical site in the patient;
wherein the first tapering point is present before said inflatable member is inflated.

28. A surgical access assembly:
a percutaneous access sheath having a first portion and a second portion, the first portion having an inner layer and an outer layer, the second portion having the inner layer, the inner layer extending longitudinally from the outer layer at an intersection of the first portion and the second portion, the inner layer adapted to have a first cross-sectional profile along at least part of a length of the second portion;
an insertion sheath releasably housing at least a portion of the second portion, the releasable sheath having at least one perforation, the insertion sheath further comprising:
a proximal section;
a restraint section;
a distal section; and
a first tapering point located at a transition between said proximal section and said restraint section, said first tapering point causing a reduction in the cross-sectional profile of said insertion sheath to a smaller crass-sectional profile of said restraint section and wherein said restraint section retains a portion of the inner layer in the first cross-sectional profile; and
an inflatable member positionable inside the percutaneous access sheath, the inflatable member positioned inside the second portion and inflated to a second cross-sectional profile wherein said second cross-sectional profile is greater than said first cross-sectional profile;
wherein the first tapering point is present before said inflatable member is inflated.

29. The surgical access assembly of claim 28 wherein the insertion sheath being adapted to tear along the at least one perforation to assist the removal of the insertion sheath from the percutaneous access sheath after insertion of the surgical access assembly into a patient.

30. The surgical access assembly of claim 28 further comprising:
a deployment catheter wherein the inflatable member is positionable in the deployment catheter, and
wherein the percutaneous access sheath defines an axial lumen and the deployment catheter is positionable inside the axial lumen of the percutaneous access sheath.

31. The surgical access assembly of claim 30 wherein the deployment catheter comprises:
an inner tube and an outer tube, a portion of the outer tube forming the inflatable member; and an inflation lumen positioned between the inner tube and the outer tube for inflating the inflatable member.

32. The surgical access assembly of claim 31 wherein the deployment catheter further comprises:

a guide wire lumen defined by an inner surface of the inner tube.

* * * * *